US005888232A

United States Patent [19]
Taylor

[11] Patent Number: 5,888,232
[45] Date of Patent: Mar. 30, 1999

[54] ULTRALIGHT MODULAR QUICK-ADJUSTING CONNECTOR

[76] Inventor: Douglas A. Taylor, 7823 Lovage Ct., Indianpolis, Ind. 46237

[21] Appl. No.: 795,828

[22] Filed: Feb. 6, 1997

Related U.S. Application Data

[63] Continuation of Ser. No. 346,528, Nov. 29, 1994, abandoned.

[51] Int. Cl.$^6$ ....................................................... A61F 2/62
[52] U.S. Cl. ................................. 623/38; 403/87; 403/90
[58] Field of Search ................................ 623/38; 403/87, 403/90, 82

[56] References Cited

U.S. PATENT DOCUMENTS

| | | | |
|---|---|---|---|
| 223,752 | 1/1880 | Owen | 403/87 |
| 409,311 | 8/1889 | Snyder | 623/38 X |

(List continued on next page.)

FOREIGN PATENT DOCUMENTS

| | | | |
|---|---|---|---|
| 1241623 | 8/1960 | France | 403/90 |
| 2410998 | 8/1979 | France | 623/38 |
| 309815 | 12/1918 | Germany | 623/57 |
| 1026803 | 7/1983 | U.S.S.R. | 623/38 |
| 118170 | 8/1918 | United Kingdom | 403/90 |
| 2024926 | 1/1980 | United Kingdom | 403/90 |
| 2114447 | 8/1983 | United Kingdom | 623/38 |
| 2162069 | 1/1986 | United Kingdom | 623/38 |
| 2169207 | 7/1986 | United Kingdom | 623/38 |
| 9115169 | 10/1991 | WIPO | 623/38 |
| 93017640 | 9/1993 | WIPO | 623/38 |

OTHER PUBLICATIONS

Ohio, Willow Wood Company, *Silhouette Lightweight Prosthesis Kit*, Oct., 1994 (2 pages).
Ohio Willow Wood Company, *Silhouette lightweight Prosthesis—Fabrication instructions*, Oct. 1, 1994 (11 pages).
United States Manufacturing Company, *USMC's OK–BK System* (1 page).
United States Manufacturing Company, *Modular Titanium Components*, © 1992 USMC (2 pages).
Fillauer, Inc., *Stability–Vision–Innovation*, Dec., 1992 (6 pages).
Durr–Fillauer Orthopedic, Inc., *Durr–Fillauer's Endoskeletal Alignment System*, May, 1992 (4 pages).
Becker Orthopedic, *The Coupler*™ (1 page).
Ohio Willow Wood Company, *The Human Touch Series—Below Knee Instruction Manual*, Dec., 1992 (34 pages).
Ohio Willow Wood Company, *The Human Touch Series—Below Knee Instruction Manual*, Jul., 1994 (40 pages).
Ohio Willow Wood Company, *BK Endoskeletal Components Overview* (23 pages).
Ohio Willow Wood Company, *The Human Touch Series*, May 4, 1994 (11 pages).

(List continued on next page.)

*Primary Examiner*—David H. Willse
*Attorney, Agent, or Firm*—Daniel L. Boots

[57] ABSTRACT

A prosthetic system including a novel connector is provided comprising a first prosthetic member such as a pylon tube having a first male end, an extending member such as a prosthetic bolt having a proximal end and a distal end, the male end of the first prosthetic member having an opening therein for receiving the distal end of the bolt, and a second prosthetic base member have a female contact surface for receiving the male end of the first prosthetic member and for anchoring the proximal end of the bolt. The bolt is generally fixed in position relative to the second prosthetic member while the first prosthetic member is movable relative to the second prosthetic member. The bolt may be tightened to releasably lock the first prosthetic member in a fixed position relative to the second prosthetic member. The male end of the first prosthetic member is preferably convexly hemispherical, and the female contact surface of the second prosthetic member preferably includes a concavely hemispherical seat for receiving the male end of the first prosthetic member.

21 Claims, 5 Drawing Sheets

U.S. PATENT DOCUMENTS

| | | | |
|---|---|---|---|
| 1,283,093 | 10/1918 | Critchley . | |
| 3,400,408 | 9/1968 | Garcia | 623/38 X |
| 3,422,462 | 1/1969 | Finnieston . | |
| 3,649,968 | 3/1972 | Prahl . | |
| 3,659,294 | 5/1972 | Glabiszewski . | |
| 3,790,965 | 2/1974 | Gelbenegger . | |
| 3,906,552 | 9/1975 | Weber . | |
| 4,155,590 | 5/1979 | Cumningham | 403/87 X |
| 4,157,876 | 6/1979 | DiGiulio | 403/90 |
| 4,161,042 | 7/1979 | Cottingham et al. . | |
| 4,177,525 | 12/1979 | Arbogast et al. . | |
| 4,283,800 | 8/1981 | Wilson . | |
| 4,302,856 | 12/1981 | May . | |
| 4,463,459 | 8/1984 | Shorter et al. . | |
| 4,475,546 | 10/1984 | Patton | 606/57 |
| 4,536,898 | 8/1985 | Palfray | 623/33 |
| 4,608,054 | 8/1986 | Schroder | 623/39 |
| 4,865,612 | 9/1989 | Arbogast et al. | 623/55 |
| 4,969,911 | 11/1990 | Greene | 623/38 |
| 5,004,477 | 4/1991 | Palfray | 623/53 |
| 5,013,325 | 5/1991 | Rennerfelt | 623/38 |
| 5,047,063 | 9/1991 | Chen | 623/38 |
| 5,062,859 | 11/1991 | Naeder | 623/55 |
| 5,133,777 | 7/1992 | Arbogast et al. | 623/38 |
| 5,139,524 | 8/1992 | Aulie et al. | 623/38 |
| 5,156,631 | 10/1992 | Merlette | 623/52 |
| 5,201,775 | 4/1993 | Arbogast et al. | 623/38 |
| 5,249,766 | 10/1993 | Vogt | 248/181 |
| 5,314,499 | 5/1994 | Collier, Jr. | 623/47 |
| 5,405,410 | 4/1995 | Arbogast et al. | 623/47 |

OTHER PUBLICATIONS

Ohio Willow Wood Company, *Carbon Copy II Foot Pyramid* (2 pages).

Ohio Willow Wood Company, *The Human Touch Series Adjustable Components* (2 pages).

Southern Prosthetic Supply, *USMC Modular System* (2 pages).

Pel Supply Co., *U.S.M.C Carbon Composite BK System* (1 page).

Ohio Willow Wood Company, *BK Endoskeleton Components Overview*, Nov. 1992 (9 pages).

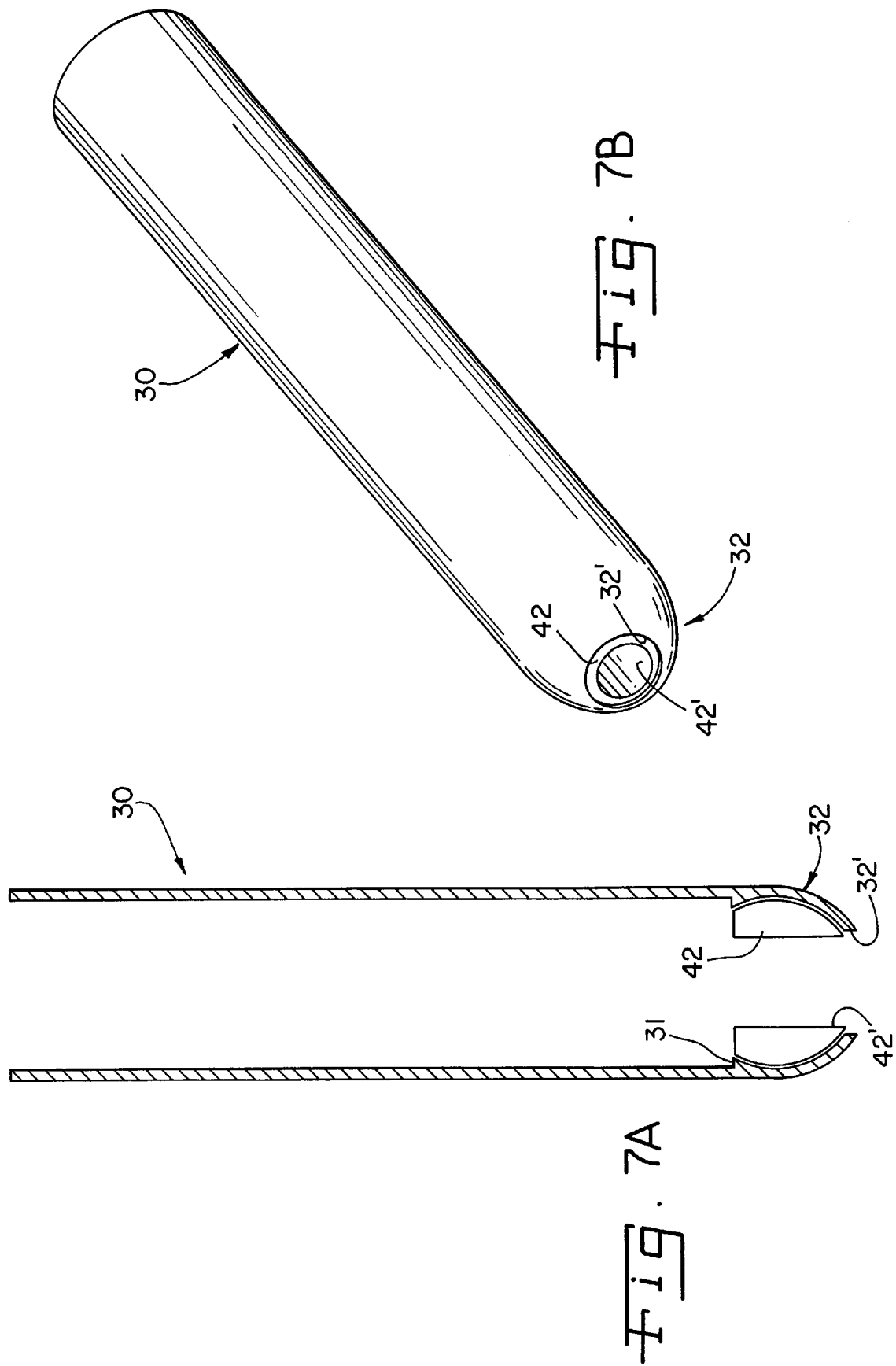

ULTRALIGHT MODULAR QUICK-ADJUSTING CONNECTOR

This application is a continuation of application Ser. No. 08/346,528, filed Nov. 29, 1994, now abandoned.

TECHNICAL FIELD

This invention relates to connectors and, more particularly, to an ultralight modular quick-adjusting connector system especially useful in prosthetic limb systems.

BACKGROUND ART

Prosthetic limbs must be custom made because of the individual deviation in height and weight of each person and the individual idiosyncratic physiological condition of the person's residual limb including, but not limited to, the length of the residual limb, the possible weight fluctuations thereof and the atrophy of the limb that typically occurs after amputation. Moreover, the residual limb commonly changes shape due to the changes in swelling during the healing process. Because each prosthetic limb must be custom made to accommodate these individual conditions, such limbs cannot be mass produced, which considerably increases their costs.

In fitting a patient with a prosthesis following an amputation of a lower limb, the prosthesis must ensure the prosthesis swings substantially in the sagittal plane during walking by the patient. The body of the patient and his attitude or gait when walking typically require certain adjustments in the relative positioning of various components of the prosthetic device. These adjustments are frequently made in two orthogonal places—the anterior-posterior plane and in the lateral-medial plane. During the initial fitting, the prosthesis typically builds up an artificial limb utilizing adjustable elements in accord with the length and orientation of the patient's body. The final prosthetic device, however, is commonly permanently fixed at the various joints, thus precluding any further or later adjustment. An improper adjustment means that the patient wearing the leg prosthesis binds the leg unnaturally, which results in an unnatural movement pattern during walking. Nevertheless, even with the best initial fitting, the patient, while adapting to the artificial limb, may change his stance or gait to the extent that, for example, flexion of the knee joint no longer occurs in the sagittal plane. This is difficult to accommodate in a permanently bonded artificial limb, particularly when the prosthetic socket, normally molded to fit the patient's residual limb, is fixed to the remaining portion of the prosthesis.

Some adjustable fittings or connectors are available in the prior art to permit separation of the molded socket from the prosthesis to permit incremental rotation of the inferior portion of the prosthesis relative to the socket. Certain prior art devices also include later adjustment facilities to allow for the adjustment of the angular attitude and position relative to the load line of the pylon tube after the prosthesis has been in use for some time. (The load line is an imaginary line extending between the foot joint and the knee along which, ideally, the body weight acts.)

Various prosthetic joints or connectors for an endoskeletal artificial leg are also well known. Such joints typically comprise an adjustable link designed to interconnect adjoining members of a prosthetic limb, such as a residual limb support, i.e., a prosthetic socket and a thigh member, a knee joint and a lower leg member, or at the ankle for connecting the lower end of a prosthesis to an artificial foot. The upper and/or lower portions of such an artificial joint is commonly provided with some means for adjustment.

One prior art system is the ball-and-socket type that permits appropriate flexion of the shin relative to the foot. Exemplary of such technology is Shorter et al., U.S. Pat. No. 4,463,459. Such ball-coupling arrangements, however, are generally of a heavy construction in order to achieve the required strength and stability while in use. The resulting heavy weight, however, is undesirable to the wearer as it causes undue energy expenditure and lack of control of the prosthetic device.

Moreover, various types of angle adjustment units are also known for adjusting the longitudinal axis of a prosthesis. Present modular prosthetic limb components commonly utilize frusto-pyramidal bosses and screws to affect angular adjustments in alignment and speed assembly procedures. Typically, a series of metal adapters and aluminum tubes are connected together to assembly the prosthetic structure. Such adapters employ only a relatively small surface area to interface parts. Consequently, heavy metals such as steel or titanium are typically used in such amounts that increase the weight of the device significantly. Thus, though such devices are manufactured for convenient later adjustability, they are not designed for minimum weight. Furthermore, these angular adjustment units are capable of transmitting only a relatively small momentum and are expensive to design and manufacture.

In any prosthetic device, it is desirable to decrease the weight of the elements in order to decrease the strain placed on the patient. Elimination of any unnecessary parts and the use of lighter materials to replace heavier components such as the connector joint or the pylon tube are particularly desirable objectives.

Some modular componentry, on the other hand, is relatively light in weight but lacks the desired adjustability. In the case of a modular below-knee (BK) prosthesis, the lightest a prosthetic device can be is about 3 pounds. For an above-knee (AK) prosthesis, the minimal weight is about 6 pounds to maintain full adjustability. This factor is significant because a prosthesis is considered "dead weight" (without sensation) to the patient. During the swing phase of gait, the prosthesis will tend to drop away from the patient's residual limb due to its weight. During the heel strike and stances phases, the prosthesis will tend to move upward until pressure equilibrium is attained. This results in considerable "pistoning" (up and down piston-like movements) of the prosthesis due to gravity, especially in the case of poor suspension of the prosthetic device from the residual limb. This pistoning action leads to lack of control and reduced proprioception. Reduction in weight can reduce or eliminate these problems by reducing the moment of inertia required to accelerate and decelerate the prosthesis.

Accordingly, there remains a need for a prosthetic device that is light in weight while sufficiently strong, that is economical to manufacture, and that readily allows for later adjustment of the device without damaging the physical integrity of the prosthetic device.

SUMMARY OF THE INVENTION

This invention presents a ultralight modular connector system especially useful in a modular prosthetic system that decreases the energy expended by the wearer and provides better comfort, control and mobility, thereby enhancing the quality of life of the amputee patient. The invention consolidates parts, reduces the amounts of heavy metals to a minimum, and significantly simplifies the alignment process. Moreover, the reduced weight of the resultant prosthetic device reduces the problems caused by the pistoning action of the device by reducing the moment of inertia required to accelerate/decelerate the device, which also leads to less random movement between the residual limb and the socket, thereby increasing the comfort to the wearer.

This invention provides a quick-adjusting modular prosthetic system including a first connector connected to one end of a tube member and a second connector connected to the opposite end of the tube member. When employed in such a prosthetic system, the first connector interconnects the tube member, such as a prosthetic pylon, to a socket for receiving a residual limb and the second connector interconnects the pylon to a prosthetic foot.

More particularly, the modular prosthetic system comprises a first prosthetic member such as a pylon tube having a first male end, an extending member such as a prosthetic bolt having a proximal end and a distal end, the first end of the first prosthetic member having an opening therein for receiving the distal end of the bolt, and a second prosthetic member for anchoring the proximal end of the prosthetic bolt. The prosthetic bolt is generally fixed in position relative to the second prosthetic member while the first prosthetic member is movable relative to the second prosthetic member. The prosthetic bolt may be tightened to releasably lock the first prosthetic member in a fixed position relative to the second prosthetic member. The first male end of the first member is preferably convexly hemispherical, and the second prosthetic member includes a concavely hemispherical seat for receiving the male end of the first prosthetic member. Thus, the novel connector system of this invention comprises a ball, a radiused-end socket and a seat that employs the single prosthetic bolt to lock and unlock the connector.

All angular and rotational adjustments can be readily made by simply accessing the securing prosthetic bolt. When in use in an artificial BK limb system, all such adjustments are available from outside the foam cover of the prosthesis. Moreover, heel height adjustments are now made available to the patient by this invention.

The connector system of the invention can also be employed in a light-weight structural network that can be collapsed and readily transported, such as those employed in the construction of space station structures. Ultralight collapsible wheelchairs are another possible application.

Other novel features and advantages of the invention will be apparent from the drawings and detailed description that follows.

BRIEF DESCRIPTION OF THE DRAWINGS

FIGS. 7A and 7B are cross-section and perspective views of a novel tubular member employed with the prosthetic connector system of this invention.

BEST MODES FOR CARRYING OUT THE INVENTION

Figure 1:
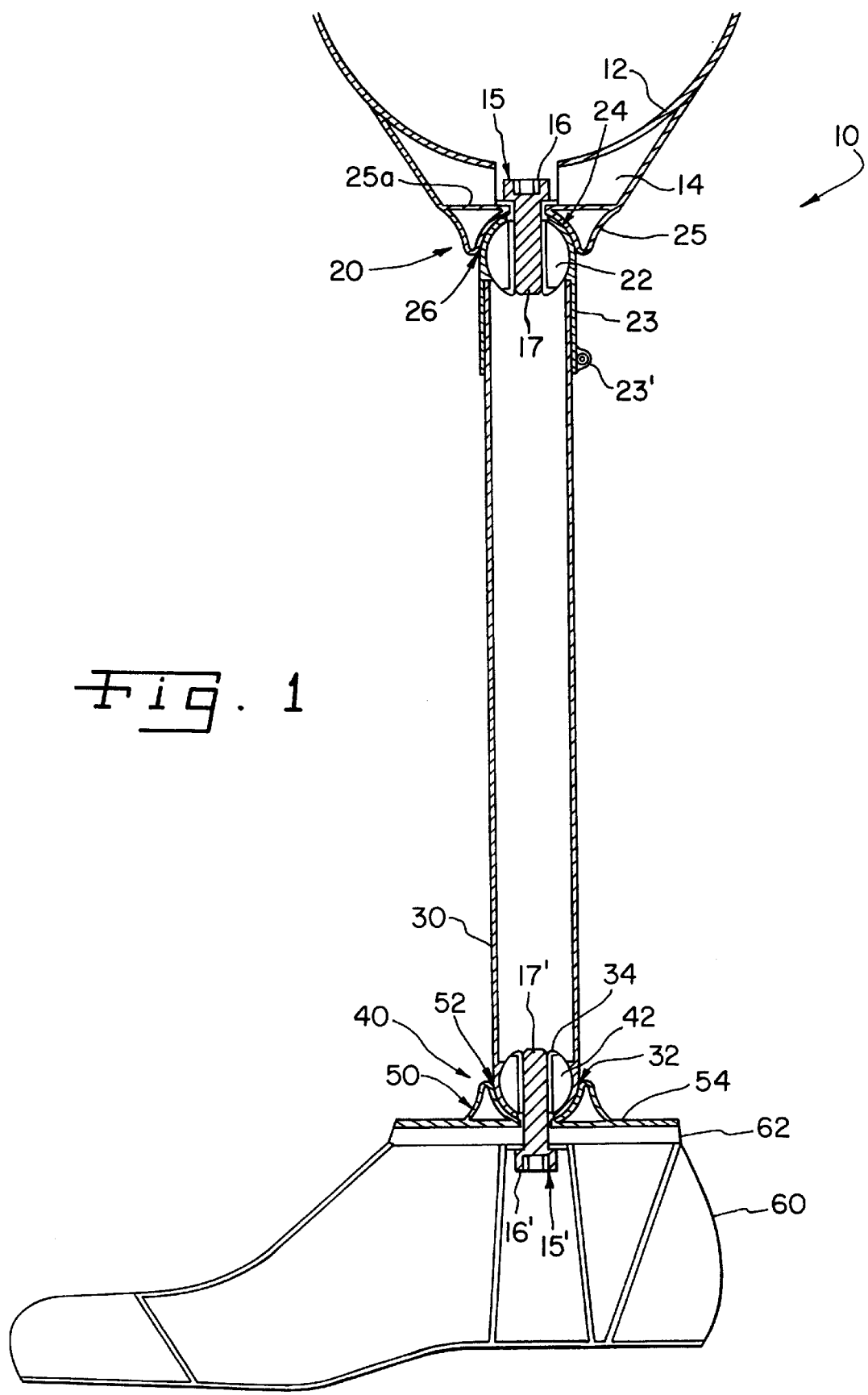
FIG. 1 is a cross section of a prosthetic BK leg system constructed in accordance with the invention.

Referring now to the drawings wherein like reference numerals designate identical or corresponding parts throughout the various views, FIG. 1 shows a prosthetic device 10 constructed in accordance with the present invention. Prosthetic device 10 shown in FIG. 1 is designed for a below-the-knee (BK) amputation and thus includes no knee joint. However, the claimed invention is not limited to any particular limb for which a prosthesis is needed, nor is the invention necessarily limited to prosthetic systems.

Device 10 includes a prosthetic socket 12 for receiving a residual limb therein, a foam core 14 to provide a light-weight core for the inner and outer layers, a first connector system 20 interconnecting the socket 12 to the upper end of a prosthetic tube or pylon 30, and a second connector system 40 interconnecting the lower end of pylon 30 to a prosthetic foot 60.

Figure 3:
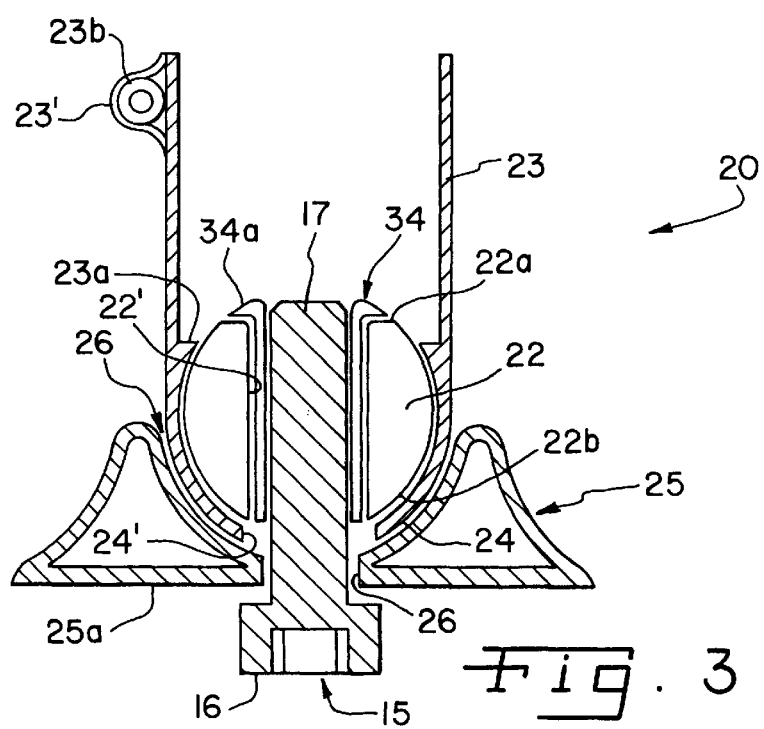
FIG. 3 is an enlarged detail cross-section of a further embodiment of a connector system of this invention.

As shown in FIGS. 1 and 3, connector system 20 of the invention more specifically comprises a spherical element such as a ball 22, a first prosthetic member defined by a tubular pylon adapter 23 having a first male end defined by a convexly hemispherically shaped end 24, and a second prosthetic member 25 having a concavely hemispherically (bowl-like) shaped female contact surface 26 for receiving therein the male end 24 of adapter 23. Connector 20 further includes an extending member 15 defined by a prosthetic bolt having a proximal end 16 and a distal end 17. The distal end 17 extends through an opening 26 provided in the second prosthetic member 25 and an opening 24' disposed in the male end 24 of adapter 23 to be received through a diametrical bore 22' provided in ball 22. Distal end 17 of bolt 15 is externally threaded and is received within an internally threaded insert 34 disposed within the bore 22' of ball 22.

Ball 22 has a planar surface 22a on one side and threaded insert 34 has a radial shoulder 34a, the underside of which abuts the planar surface 22a of ball 22. Ball 22 has a spherical surface 22b which bears against the concavely spherical interior surface of radiused end 24.

Adapter 23 also includes a shoulder 23a, which retains ball 22 within the first end 24 of adapter 23, and as shown in FIG. 1, provides an abutment means against which the upper end of pylon 30 rests when received within adapter 23. Second prosthetic member 25 includes a base 25a that, in the connector system 20 as shown in FIG. 1, can be trimmed as needed and affixed to a limb socket 12. If desired, the entire prosthetic seat member 25 may be integrally molded in the prosthetic socket.

Adapter 23 is secured to the upper end of pylon 30 via tightening or fastening means 23' which, when tightened, decreases the diameter of adapter 23 slightly so as to increasingly bear against the upper end of the pylon 30 in a clamping fashion. Fastening means 23' includes a sleeve 23b to prevent damage to the composite material from which adapter 23 is constructed. Sleeve 23b also includes a threaded portion for receiving the threaded end of the fastener as is known in the art.

Figure 4:
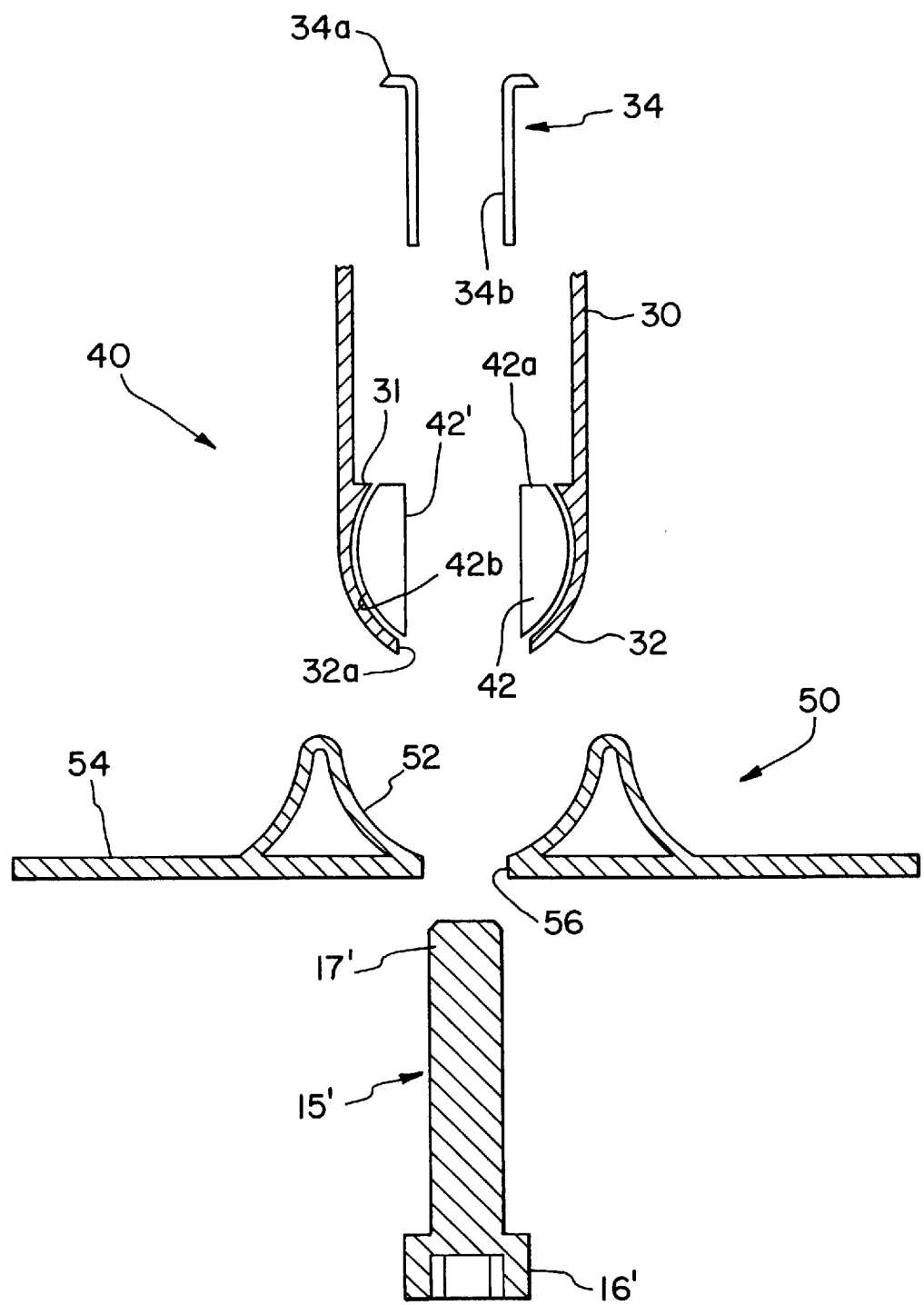
FIG. 4 is an exploded cross-section of the connector system of FIG. 2.

Connector system 40 interconnects the lower end of pylon tube 30 with the prosthetic foot 60 and is similar in structure to upper connector system 20, except system 40 includes a first prosthetic member defined by pylon 30 instead of the adapter 23 employed with upper connector system 20. Accordingly, as best shown in FIG. 4, connector system 40 includes a spherical element such as a ball 42, a first prosthetic member defined by pylon 30 having a first end defined by a convexly hemispherically shaped male end 32, and a second prosthetic member 50 having a concavely hemispherically shaped female contact surface 52 for receiving therein the male end 32 of pylon 30. Second prosthetic member 50 also includes a base 54 which can be affixed by conventional adhesives to a foot plate 62 of a prosthetic foot 60. Base 54 may be trimmed as needed to fit the dimensions of the foot plate 62 of foot 60. Alternatively, the entire prosthetic seat member 50 can be integrally molded atop a prosthetic foot.

Connector system 40, like connector system 20, includes an extending member defined by a prosthetic bolt 15' having proximal end 16' and a threaded distend end 17'. Bolt 15' is slightly longer than bolt 15 of connector 20 to accommodate the foot plate 62 of foot 60 as shown at 15". The distal end 17' extends through an opening 56 provided in the second prosthetic member 50, and through an opening 32a provided in the male end 32 of pylon 30 to be received through a diametrical bore 42' provided in ball 42. Distal end 17' of bolt 15' is externally threaded and is received within insert 34 disposed within the bore 42'. Insert 34 is provided with internal threads at 34b.

Ball 42 also has a substantially planar surface 42a on one side against which abuts the radial shoulder 34a of insert 34. Ball 42 includes a spherical surface 42b which bears against the concavely spherical interior surface of radiused end 32 of pylon 30. End 32 also includes an internal lip or shoulder 31 which retains ball 42 within the first end 32 of pylon 30.

Figure 2:
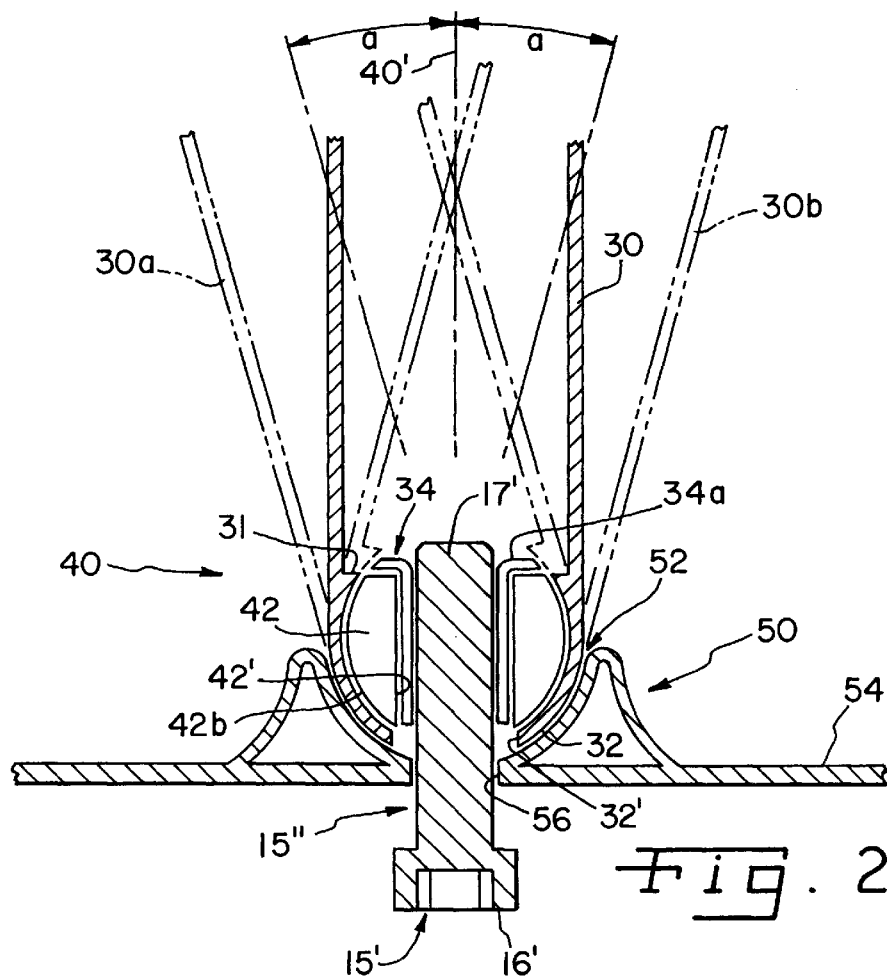
FIG. 2 is an enlarged detail cross-section of a connector system of this invention.

The tightening of bolt 15' applies a clamping force on the radiused end 32 of pylon 30 against seat surface 52. This provides prevailing torque to prevent the pylon 30 from tilting when a bending force is applied. When bolt 15' is loosened, the pylon tube 30 may be tilted or rotated in any direction to provide quick and easy adjustment. As shown in FIG. 2, tube 30 is tiltable up to an included angle "a" of approximately 15 degrees as shown by phantom FIGS. 30a and 30b. Pylon 30 may be rotated through a full 360 degree pattern. The spherical exterior surface of the male end 32 slides between the mating hemispherical surfaces 42b and 52 of ball 42 and prosthetic seat 50, respectively, as best seen in FIG. 4. To this end, opening 32a in the male end 32 of pylon 30 should be sufficiently larger in diameter than bolt 15' to allow for the pylon 30 to be tilted; otherwise, if the circumferential edge of opening 32a abutted against or was distanced only slightly from the bolt shank, such an arrangement would in effect "lock" the end 32 of the pylon 30 and prevent any tilting movement of pylon 30.

During any movement of pylon 30, the orientations of ball 42 and seat 50 remain stationary relative to a longitudinal axis 40' of connector 40 due to the fixed orientation of bolt 15' with respect to the prosthetic seat 50 and ball 42. The pylon 30 may then be readily locked in a fixed position relative to the seat 50 and axis 40' by tightening bolt 15' to threadably engage insert 34.

Connector system 20 works in a substantially similar fashion wherein the tightening of bolt 15 engages the threaded insert 34 to pull the insert toward the proximal end 16 of the bolt, which clamps the male end 24 of adapter 23 between the ball 22 and the contact surface 26 of seat 25. Connector system 20 includes adapter 23 so that in custom fitting a patient, the prosthesis determines the appropriate length required for pylon 30 and cuts off any unnecessary length. This allow the pylons of this invention to be manufactured in standard lengths that may then be sized as needed when fitting the patient.

After the prosthetic has been fitted and all angular adjustments made to accommodate the particular physiological characteristics of the patient, an urethane or epoxy adhesive may be applied if desired at the interface of the male ends 24, 32 of adapter 23 and pylon 30, respectively, and the contact surfaces 26 and 52 of prosthetic seats 25 and 50, respectively, to further ensure the fixed rigidity of the connections for the prosthetic device 10.

The preferred material used for the ball 22, 42 is a thermoplastic material, such as DELRIN or nylon, provided with a threaded insert 34, or the ball can be constructed of a light-weight metal such as aluminum, which is then diametrically bored and threaded ⅜" ½-16—a standard thread for a prosthetic bolt. The thermoplastic ball is preferably ½" to 1½" in diameter depending on the patient. In the prosthetic system 10 of FIG. 1, the upper ball 22 preferably has a diameter of about 1⅛ inches, while the lower ball 42 has a diameter of about 1 inch. Children typically use small components and heavy or active adults typically use larger components. The thermoplastic ball is machined flat on one side to provide a substantially planar surface (22a, 42a) and drilled perpendicular to that plane to provide a diametrical bore (22' and 42'), which accommodates the T-nut-type threaded insert 34. The insert can be pressed in, bonded with adhesive, ultrasonically welded, or the like. When the fastening bolt is tightened, the plastic ball is plastically deformed to exert pressure on the inside radius of the male end of the pylon tube to provide the clamping force which locks tube 30 or adapter 23 in position.

The pylon tube 30, shown separately in FIGS. 7A and 7B, is formed from winding composite filaments on to a tooling rod (mandrel) preferably made of polished steel, a plastic material, or silica sand/PVA mixture, using a NC-controlled filament winding process. Alternatively, the pylon tube 30 can be constructed of pre-impregnated materials that can be hand-laid on the prosthetic mold. Pylon 30 has a thickness of about 0.060 inches. The tooling mandrel has flat ends (90° to long axis), threaded studs on each end that are compatible with the threaded insert 34, and a slot in the middle with a replaceable bushing that can be cut against with a composite machining tool. The mandrel may unscrew at its mid-part for easy part removal. A ball (22, 42) is screwed onto each end of the mandrel with the top shoulder 34a of the insert 34 abutting against the flat end of the mandrel. A bushing is then applied over the threaded end of the mandrel against the bottom of the ball, which is beveled on its outside diameter to retain the fiber filaments at the radius end. The bevel is designed to the required radius and thickness as the expected composite thickness. The inside diameter of the bushing is also beveled so that the bolt 15 that screws into the insert is allowed clearance at openings 24' and 32' as the tube tilts up to 15°. The bushing is retained by a nut or a threaded washer.

The mandrel is preferably the same diameter as the ball and has a groove between the bottom half of the ball and the end of the mandrel. This groove is filled with composite during the winding process creating a reverse radius defining retaining lip or shoulder 23a and 31 that permanently retains the ball within the first end of the tube 32 after winding is completed. The mandrel will then have a two to four degree draft angle from the mid-shaft toward each end to facilitate the removal of the mandrel from the tube. The threaded insert 34 in the ball also helps the mandrel to be pushed out as it is unscrewed. The mandrel and two balls will have a geometry identical to a mandrel for a filament wound pressure vessels (except for the groove). This configuration makes it possible to manufacture two ball-tube components concurrently if desired, thus making higher production levels possible.

While winding patterns already exist for this geometry, the winding patterns employed to construct the pylon tube 30 of this invention can be varied many ways. For example, a variety of hoop and helical winding patterns can be used to achieve strength to resist tensile, compressive, and bending moments on the pylon tube, as well as clamping pressures on the radiused end and top of the tube. Carbon-epoxy and fiberglass-epoxy are preferred materials in the construction of pylon tube 30 and adapter 23. If necessary, the tube can be wound with extra material so that the tube can be machined to the desired outside diameter.

A shorter version of the two-ball mandrel with a diameter tolerance such that the finished part will fit over the tube at the top is needed to fabricate a two ball-tube adapter. The tube adapter will have a screw, sleeve, and nut wound into it. After the wound parts are removed from the mandrel, the tube adapter is cut longitudinally so that the sleeve and screw head will be on the opposite side of the slot from the nut. This will allow the screw to reduce the circumference of the tube adapter, thus creating a clamping force on the tube. This will allow length adjustments to the system by cutting the tube as needed to custom fit the patient.

The prosthetic seat (25, 50) is made of a composite, a thermoplastic, a light-weight metal, or a combination of those materials. The weight bearing contact surfaces 26, 52 of the seats are toleranced to fit the male radiused ends of the pylon tube and the adapter. Clearance and reverse radius will be provided to allow the tube to tilt up to 15°. A hard point is necessary at openings 26, 56 to prevent the fastening bolt from collapsing or damaging the seat from where it applies pressure about the circumferential area adjacent the openings.

In operation, the existence of two connector mechanisms 20, 40, one at the foot and one at the limb socket of prosthetic device 10, allows for all of the necessary adjustments in prosthetic alignment procedures to be made. These adjustments include primarily movement of the upper limb socket 12 in relationship to the foot 60. Such movements are anterior or posterior tilt, medial or lateral tilt, anterior or posterior slide, medial or lateral slide, and internal or external rotation. Length adjustments are, as noted above, made by removing the adapter 23 and cutting the pylon tube 30 as needed. After alignment adjustments are made, the bolts beneath the foot and in the bottom of the socket are tightened to "lock-in" the alignment of the prosthetic device 10. One very helpful feature is that with a hex-head wrench, the patient is able to adjust the heel height of the foot 60 himself to fit different shoes. This has previously been accomplished by using lifts placed in the shoe. Moreover, later adjustments to the alignment of device 10 maybe readily made via the two bolts 15 and 15' without disrupting the cosmesis of the prosthesis 10. This gives an amputee adjustable heel height which allows for more shoe choices and for greater comfort in shoeless walking.

Figure 6A:
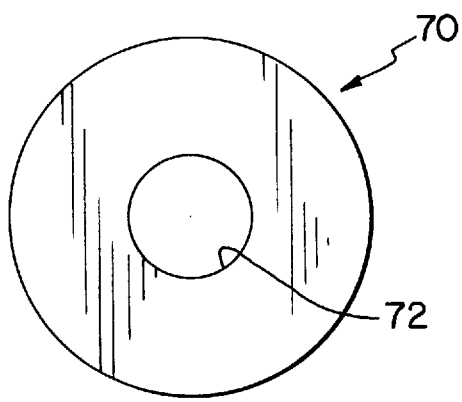
FIGS. 6A and 6B are top plan and perspective views, respectively, of a friction-enhancing element that can be utilized with the connector system of this invention.
Figure 6B:
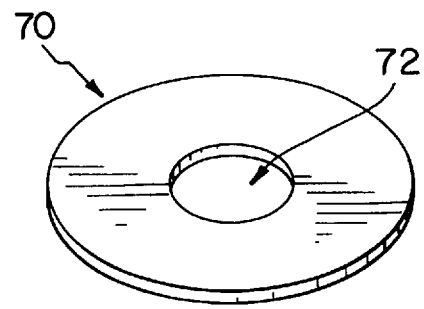

The interface between the radiused end of the first prosthetic member (tube 30 or adapter 23) and the second prosthetic member seat 25 and 50 is of concern because these surfaces have a great potential for wear and slippage. If desirable, an interface material, such as an elastomeric or neoprene washer 70 shown in FIGS. 6A and 6B can be employed therebetween. Such friction-enhancing means like elastomeric washer 70 can include an opening 72 through which the fastening bolt extends.

Alternatively, surface finishes such as polyurethane coats can be employed to protect the composite tube and create enough friction at the interface to prevent slippage during walking. Moreover, energy storing feet have a tendency to increase the bending moment at the ankle (the location of the lower connector mechanism 40), which increases the potential for slippage. This requires the prosthesis to study bolt torque settings in combination with the preferred interface materials during bending tests to achieve the right amount of prevailing torque to maintain the proper alignment of the prosthetic device during use.

Figure 5:
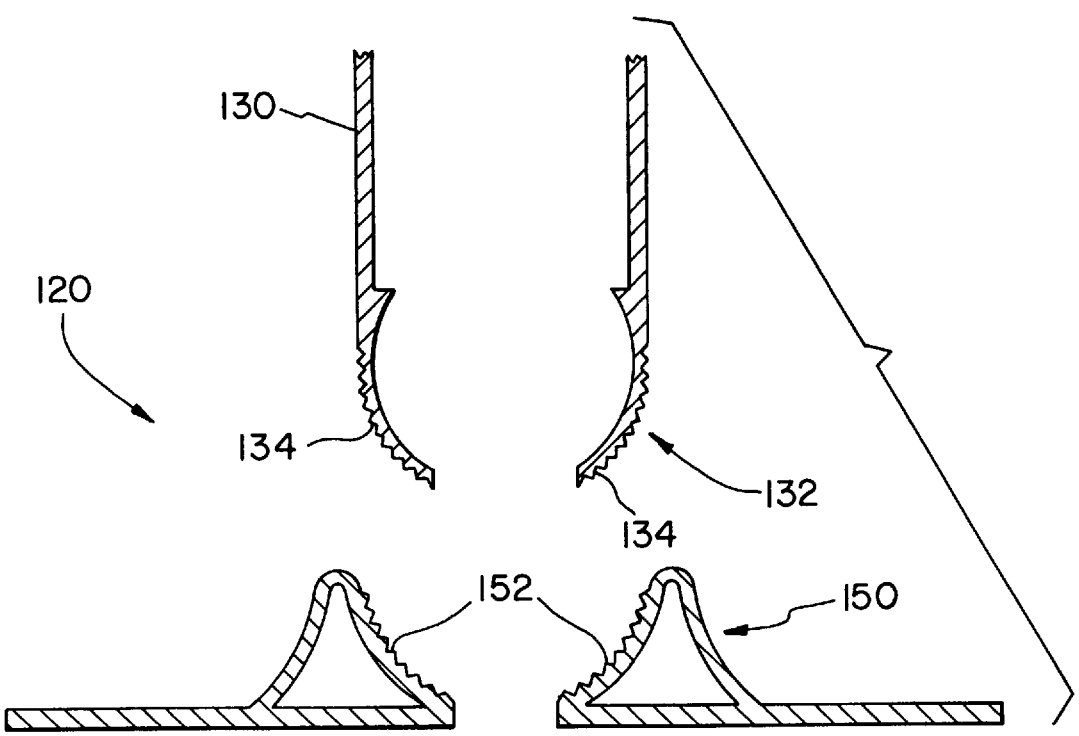
FIG. 5 is an enlarged detail cross-section of even a further embodiment of a connector system of this invention.

FIG. 5 shows a further alternative connector mechanism 120 provided by the invention wherein the exterior of first end 132 of pylon tube 130 is provided with a serrated, knurled or keyed surface 134 that interacts in an interlocking fashion with similar serrated or knurled surfaces 152 provided on the female weight bearing surfaces of prosthetic seat 150. In all other aspects, connector mechanism 120 is identical to connector mechanisms 20 and 40.

Bending tests to failure should always be performed to determine the limits for the tube and the connector mechanisms. The compressive strength of the tube and of its radiused end to failure can be tested on an Instron Model. Circumferential clamping tests should also be performed on the upper end of the tube. Impact testing of the tube is also necessary to ensure that energy released during an unintended fracture is not potentially dangerous to the patient. The prosthetic seat should be subjected to high clamping forces to test the off-axis crush strength of the seat.

The device of this invention and its novel components are a radical change in design from present technology. The device 10 for below-knee amputees as shown in FIG. 1 utilizes advanced composites and materials with an ultralight foot and prosthetic socket that results in a prosthetic device as light as 1.3 pounds or less. Such a drastic reduction in weight results in a reduction in energy expenditure and fatigue, better control, and increased mobility for the patient, which could mean the difference between walking or not walking for patients with low energy reserves, particularly geriatric patients. Moreover, by adding a small amount of additional composite material to the pylon section as needed, the strength of the system can be greatly increased improved, thereby making the device safe for very heavy and active patients. Smaller tooling of the same geometry can also be utilized to fit a device of this invention to pediatric patients.

Thus, this invention has a significant advantage over present systems in being able to provide lighter modular prosthetics with much higher strength. Another significant advantage is that all adjustments to the prosthetic alignment are available outside the cosmesis of the prosthesis. Development of other components such as ultralight knees, energy-storing pylons, and hip joints as possible because of this invention.

Although the device provided by the present invention has been described with a preferred embodiment, those skilled in the art will understand that modifications and variations may be made without departing from the scope of this invention as set forth in the following claims. Accordingly, such modifications and variations are considered to be within the purview and scope of the claims.

It is claimed:

1. A connector system for a prosthetic system, comprising:

first prosthetic means defined by a prosthetic pylon having an integral first end defined by a convexly protruding surface partially closing said first end, said protruding surface defining a concavely spherical interior surface and a convexly spherical exterior surface;

means permanently carried internally of said prosthetic pylon near the first end thereof by a radially inwardly extending abutment in an abutting relationship against the interior surface of the protruding first end of said prosthetic pylon, said internal means having at least one convexly spherical bearing surface and being free to rotate within the end of said prosthetic pylon, said internal means being permanently retained within said pylon while the prosthetic connector system is in an unassembled state;

an extending member having a proximal end and a distal end, said first end of said prosthetic pylon having an opening disposed therein for receiving the distal end of said extending member; and second prosthetic means affixable to a socket for a residual human limb or to a prosthetic foot or knee for anchoring the proximal end of said extending member, said extending member being generally fixed in position relative to said second prosthetic means, said prosthetic pylon being movable relative to said second prosthetic means, and said extending member being operable to releasably secure said prosthetic pylon in a fixed position relative to said second prosthetic means whereupon the at least one bearing surface of said internal means engages the interior surface of the first end of said prosthetic pylon, which in turn causes the exterior surface of said prosthetic pylon to bear against said second prosthetic means releasably locking said prosthetic pylon and second prosthetic means in a fixed relation to each other.

2. The connector system of claim 1 wherein said second prosthetic means includes a concavely spherical surface for receiving the first end of said prosthetic pylon.

3. The connector system of claim 1 wherein the extending member threadably couples said prosthetic pylon with said second prosthetic means such that a tightening of said extending member clampingly engages the first end of said prosthetic pylon between the second prosthetic means and the at least one bearing surface of said internal means to releasably fix said prosthetic pylon in position relative to said second prosthetic means.

4. The connector system of claim 1 wherein the internal means of said prosthetic pylon comprises a substantially spherical member having a diametrical bore extending therethrough.

5. The connector system of claim 4 further comprising internally threaded means arranged within the bore of said spherical member, and wherein said extending member includes an externally threaded portion adjacent the distal end thereof, wherein said second prosthetic means has a bore extending therethrough, and wherein the distal end of said extending member extends through the bore of said second prosthetic means, through the opening of the first end of said prosthetic pylon, and through the bore of said spherical member to threadably couple said prosthetic pylon and second prosthetic means.

6. The connector system of claim 1 wherein said second prosthetic means includes a central opening, and wherein the distal end of said extending member extends through the central opening of said second prosthetic means and is anchored thereat to prevent said extending member from disengaging from said second prosthetic means.

7. The connector system of claim 1 further comprising an adapter for receiving therein an opposing second end of said prosthetic pylon, said adapter including releasable fastening means such that the activation of said fastening means releasably secures the end of said prosthetic pylon within said adapter.

8. A quick-adjusting connector for an artificial limb system, comprising:

a substantially spherical element having a diametrical bore extending therethrough, said bore having internally threaded means arranged therewithin;

a prosthetic limb member having an interior, an exterior, an outwardly protruding radiused end and a bore extending through said radiused end, said radiused end having an interior surface and an exterior surface, said spherical element being permanently secured within the interior of said prosthetic limb member abutting the interior surface of the radiused end thereof while still able to rotate by a radially inwardly extending shoulder disposed internally of said prosthetic limb member, said spherical element being permanently secured within the interior of said prosthetic limb member while the quick-adjusting connector is in an unassembled state;

a prosthetic base member having a concavely spherical seat for receiving therein the radiused end of said prosthetic limb member, said prosthetic base member having a bore extending through the seat thereof; and securing means extended through the bores of said prosthetic base member, said prosthetic limb member, and said spherical element for releasably securing the radiused end of said prosthetic limb member within the seat of said prosthetic base member, thereby releasably fixing said prosthetic limb member in position relative to said prosthetic base member.

9. The adjustable connector of claim 8 wherein said spherical element has a planar surface on one side thereof and wherein the diametrical bore is disposed normally to said planar surface.

10. The adjustable connector of claim 9 wherein said threaded means comprises an internally threaded tube-like metallic insert disposed within the bore of said spherical element, said insert having a radially first prosthetic means, and through the bore of said spherical member to threadably couple said first and second prosthetic means.

11. The adjustable connector of claim 8 wherein said prosthetic limb member comprises a prosthetic pylon.

12. The adjustable connector of claim 8 wherein said prosthetic limb member comprises a tubular adapter for receiving therein one end of a tubular prosthetic pylon, said adapter including tightening means such that the activation of said tightening means causes said tubular adapter to increasingly engage and releasably secure the end of said pylon within said adapter.

13. The adjustable connector of claim 8 wherein said securing means comprises a bolt having an externally threaded shank attached to a head, said externally threaded shank engaging the internally threaded means arranged within the bore of said spherical element, said bolt head having a diameter greater than the diameter of the bore in said prosthetics base member such that said bolt head is prevented from passing therethrough.

14. The adjustable connector of claim 8 wherein said prosthetic limb member is pivotable about its radiused end relative to a longitudinal axis of said securing means upon said securing means being in an unsecured state.

15. The adjustable connector of claim 8 wherein the bore extending through the radiused end of said prosthetic limb member is disposed in general alignment with a longitudinal axis of said prosthetic limb member.

16. The adjustable connector of claim 8 further comprising friction enhancing means disposed at the interface between the radiused end of said prosthetic limb member and the seat of said prosthetic base member for increasing the friction to strengthen the fixed connection at said interface.

17. The adjustable connector of claim 16 wherein said friction enhancing means comprises serrations provided on the exterior surface of the radiused end of said prosthetic limb member and on a surface of the seat of said prosthetic base member to provide an interlocking engagement between said surfaces.

18. The adjustable connect or of claim 16 wherein said friction enhancing means comprises an elastomeric or neoprene washer having a central opening formed therein through which extends said securing means.

19. A below-knee prosthetic system comprising:
   a socket for receiving a residual human limb therein;
   a prosthetic pylon having an open end and an opposing partially closed radiused end, said radiused end having a bore therethrough;
   a prosthetic foot;
   an adapter tube having an open end and an opposing partially closed radiused end, said radiused end having a bore therethrough;
   first connection means interconnecting said socket and the open end of said prosthetic pylon; and
   second connection means interconnecting said prosthetic foot and the radiused end of said prosthetic pylon,
   said first connection means comprising:
      a substantially spherical element having a diametrical bore extending therethrough, said spherical element being rotatingly secured within said adapter tube abutting an interior surface of the radiused end thereof by a radially inwardly extending abutment disposed internally of and spaced from the radiused end of said adapter tube, said spherical element being permanently secured within said adapter tube when the first connection means is in an unassembled state;
      a base member having a seat for receiving therein the radiused end of said adapter tube, said base member having a bore extending through the seat thereof; and
      securing means extended through the bores of said base member, the radiused end of said adapter tube, and said spherical element for releasably securing the radiused end of said adapter tube within the seat of said base member, thereby releasably fixing said adapter tube in position relative to said base member.

20. The below-knee prosthetic system of claim 19 wherein said second connection means comprises:
   a second substantially spherical element having a diametrical bore extending therethrough, said second spherical element being rotatingly secured within said prosthetic pylon abutting an interior surface of the radiused end thereof by a radially inwardly extending abutment disposed internally and spaced from the radiused end of said prosthetic pylon;
   a second base member having a seat for receiving therein the radiused end of said prosthetic pylon, said second base member having a bore extending through the seat thereof; and
   second securing means extended through the bores of said second base member, the radiused end of said prosthetic pylon, and said spherical element for releasably securing the radiused end of said prosthetic pylon within the seat of said second base member, thereby releasably fixing said prosthetic pylon in position relative to said second base member.

21. A connector system for a prosthetic system, comprising:
   a prosthetic pylon adapter tube having an integral first end defined by a convexly protruding surface partially closing said first end and having a concavely spherical interior surface and a convexly spherical exterior surface;
   means permanently carried internally of said prosthetic pylon adapter tube, while the connector system is in an unassembled state, near the first end thereof in an abutting relationship against the interior surface of the protruding first end of said prosthetic pylon adapter tube by a radially inwardly extending abutment, said internal means having at least one bearing surface and being free to rotate within the end of said prosthetic pylon adapter tube;
   an extending member having a proximal end and a distal end, said first end of said prosthetic pylon adapter tube having an opening disposed therein for receiving the distal end of said extending member; and
   second prosthetic means affixable to a socket for a residual human limb or to a prosthetic foot or knee for anchoring the proximal end of said extending member, said extending member being generally fixed in position relative to said second prosthetic means, said prosthetic pylon adapter tube being movable relative to said second prosthetic means, and said extending member being operable to releasably secure said prosthetic pylon adapter tube in a fixed position relative to said second prosthetic means whereupon the at least one bearing surface of said internal means engages the interior surface of the first end of said prosthetic pylon adapter tube, which in turn causes the exterior surface of said prosthetic pylon adapter tube to bear against said second prosthetic means releasably locking said prosthetic pylon adapter tube and second prosthetic means in a fixed relation to each other.

* * * * *